(12) United States Patent
Dougherty et al.

(10) Patent No.: US 6,190,642 B1
(45) Date of Patent: Feb. 20, 2001

(54) IRRIGATING AND LAVAGE COMPOSITIONS

(75) Inventors: Emery W. Dougherty; John B. Heyde, both of York, PA (US)

(73) Assignee: Dentsply Research & Development Corp., Los Angeles, CA (US)

(*) Notice: Under 35 U.S.C. 154(b), the term of this patent shall be extended for 7 days.

(21) Appl. No.: 08/325,713

(22) Filed: Oct. 18, 1994

Related U.S. Application Data

(63) Continuation-in-part of application No. 07/432,094, filed on Nov. 6, 1989, now abandoned, which is a continuation-in-part of application No. 07/418,780, filed on Oct. 2, 1989, now Pat. No. 4,961,923, which is a continuation of application No. 07/157,672, filed on Feb. 19, 1988, now abandoned.

(51) Int. Cl.$^7$ ............... A61K 7/16; A61K 7/24; A61C 1/07; A61C 1/02

(52) U.S. Cl. ............... 424/49; 424/54; 424/55; 433/86; 433/216

(58) Field of Search ............ 424/49–58; 433/86, 433/216

(56) References Cited

U.S. PATENT DOCUMENTS

| | | | |
|---|---|---|---|
| Re. 30,675 | 7/1981 | Schole | 424/54 |
| 1,869,406 | 8/1932 | Braunlich . | |
| 2,054,742 | 9/1936 | Elbel | 167/93 |
| 3,760,799 | 9/1973 | Crowson | 128/24 |
| 3,863,628 | 2/1975 | Vit | 128/66 |
| 3,864,472 | 2/1975 | Pensak et al. | 424/54 |
| 3,887,701 | 6/1975 | Nachtigal | 424/54 |
| 3,924,335 | 12/1975 | Balamuth et al. . | |
| 3,925,543 | 12/1975 | Donohue . | |
| 3,947,570 | 3/1976 | Pensak et al. | 424/54 |
| 4,012,842 | 3/1977 | Vit | 32/58 |
| 4,022,880 | 5/1977 | Vinson et al. | 424/49 |
| 4,130,638 | 12/1978 | Dhabhar et al. | 424/55 |
| 4,137,303 | 1/1979 | Gaffar et al. | 424/52 |
| 4,150,151 | 4/1979 | Pader et al. . | |
| 4,160,821 | 7/1979 | Sipos | 424/49 |
| 4,251,507 | 2/1981 | Olson | 424/49 |
| 4,264,618 | 4/1981 | Baiocchi et al. . | |
| 4,289,755 | 9/1981 | Dhabhar | 424/52 |
| 4,315,742 | 2/1982 | Nash et al. | 433/86 |
| 4,339,432 | 7/1982 | Ritchey et al. | 424/54 |
| 4,374,122 | 2/1983 | Stroz et al. | 424/48 |
| 4,420,471 | 12/1983 | Elton et al. . | |
| 4,425,325 | 1/1984 | Ritchey et al. | 424/54 |
| 4,435,380 | 3/1984 | Pader | 424/49 |
| 4,465,661 | 8/1984 | Schmolka | 424/49 |
| 4,472,373 | 9/1984 | Ryan | 424/54 |
| 4,483,848 | 11/1984 | Cox et al. | 424/49 |
| 4,508,713 | 4/1985 | Stroz et al. . | |

(List continued on next page.)

FOREIGN PATENT DOCUMENTS

| | | |
|---|---|---|
| 961412 | 1/1975 | (CA) . |
| 988431 | 5/1976 | (CA) . |
| 1001554 | 12/1976 | (CA) . |
| 1028623 | 3/1978 | (CA) . |
| 1034505 | 7/1978 | (CA) . |
| 1042806 | 11/1978 | (CA) . |
| 1087098 | 10/1980 | (CA) . |
| 1095422 | 2/1981 | (CA) . |
| 1104939 | 7/1981 | (CA) . |
| 1116091 | 1/1982 | (CA) . |
| 1122123 | 4/1982 | (CA) . |
| 1139229 | 1/1983 | (CA) . |
| 1161860 | 2/1984 | (CA) . |
| 11168159 | 5/1984 | (CA) . |
| 2 329 728 | 1/1974 | (DE) . |
| 30 23 461 | 1/1981 | (DE) . |
| 30 01 575 | 7/1981 | (DE) . |
| 30 21 150 | 12/1981 | (DE) . |
| 0 040 738 | 2/1981 | (EP) . |
| 0 024 535 | 3/1981 | (EP) . |
| 0 079 611 | 5/1983 | (EP) . |
| 0 089 136 | 9/1983 | (EP) . |
| 0 152 836 | 8/1985 | (EP) . |
| 0 188 313 | 7/1986 | (EP) . |
| 0 265 186 | 4/1988 | (EP) . |
| 0 290 186 | 11/1988 | (EP) . |
| 2 305 965 | 10/1976 | (FR) . |
| 2364028 | 4/1978 | (FR) . |
| 2406437 | 5/1979 | (FR) . |
| 1469399 | 4/1977 | (GB) . |
| 1540648 | 2/1979 | (GB) . |
| WO 80/00057 | 1/1980 | (WO) . |
| WO 86/03674 | 7/1986 | (WO) . |

OTHER PUBLICATIONS

Barkmeier, Jabro, Latta, The Journal of Clinical Dentistry, vol. III, No. 2, 1992, Scanning Electronic Microscopic Analysis of the Local Effects of a Periodontal Scaling Gel on Selected Surfaces, pp. 39–42.

Jabro, Barkmeier, Latta, The Journal of Clinical Dentistry, vol. III, No. 2, 1992, A Clinical Evaluation of the Effects of a Periodontal Scaling Gel, pp. 43–46.

*Primary Examiner*—Shep K. Rose
(74) *Attorney, Agent, or Firm*—Dale R. Lovercheck; James B. Bieber

(57) ABSTRACT

Irrigants to be used with vibratory scaling apparatus and lavage are provided. The irrigants of the invention are characterized in that they contain medicaments for the treatment of conditions in the mouth and have a viscosity and deliquescence adapted to substantially optimize the efficiency of the apparatus. The irrigants are formulated so that they have minimal stickiness on drying, minimal foaming and do not gum-up the apparatus in which they are used. Also provided is a method for treating dental diseases comprising applying the irrigants of the invention through a vibratory scaring apparatus to substantially optimize the efficiency of said apparatus and to substantially optimize destruction and removal of infectious bacteria using said apparatus and the removal or inactivation of endotoxins derived from bacteria or the host.

43 Claims, No Drawings

U.S. PATENT DOCUMENTS

| | | | |
|---|---|---|---|
| 4,522,806 | 6/1985 | Muhlemann et al. | 424/52 |
| 4,545,979 | 10/1985 | Ambike et al. | 424/52 |
| 4,550,018 | 10/1985 | Ambike et al. | 424/52 |
| 4,582,702 | 4/1986 | Grollier | 424/52 |
| 4,584,189 | 4/1986 | Leipold | 424/54 |
| 4,601,900 | 7/1986 | Noponen et al. | 424/54 |
| 4,622,220 | 11/1986 | Frosch | 424/49 |
| 4,657,758 | 4/1987 | Goldemberg et al. | 424/49 |
| 4,666,708 | 5/1987 | Goldemberg et al. | 424/49 |
| 4,701,223 | 10/1987 | Eoga | 134/2 |
| 4,719,100 | 1/1988 | Frosch | 4424/49 |
| 4,767,615 | 8/1988 | Geho et al. | |
| 4,770,634 | 9/1988 | Pellico | 433/217.1 |
| 4,800,095 | 1/1989 | Carroll et al. | 426/548 |
| 4,843,099 | 6/1989 | Gaffar et al. | |
| 4,847,070 | 7/1989 | Pyrz et al. | |
| 4,961,923 | 10/1990 | Heyde | 424/49 |
| 5,032,388 | 7/1991 | Tikkanen . | |

IRRIGATING AND LAVAGE COMPOSITIONS

This is a continuation-in-part of Ser. No. 07/432,094 filed Nov. 6, 1989 now abandoned which is a continuation-in-part of Ser. No. 07/418,780, filed Oct. 2, 1989 now U.S. Pat. No. 4,961,923 which was a continuation of Ser. No. 07/157,672, filed Feb. 19, 1988 now abandoned.

The present invention relates especially to irrigants for use in mechanical apparatus for scaling teeth to debride and cleanse them of plaque, plague constituents and calculus, in order to mitigate the effects of periodontal diseases.

Periodontal diseases are characterized by chronic inflammation and loss of epithelial fibrous attachment between the tooth and the gum, i.e. between soft and hard tissues. The level of the attachment of the gum to the tooth is normally at the junction of the enamel and cementum, but decreases in response to the chronic inflammatory process initiated by infection with gram-negative organisms which may be found in plaque accumulations. As the level of the attachment decreases, a pocket is formed which enhances accumulation of gram negative anaerobic bacteria, favoring additional loss of gingival attachment and the enlargement of the pocket. Studies have shown that bone loss around the tooth root follows, but lags behind attachment loss. Periodontal diseases are thus typified by loss of attachment and bone which eventually may lead to tooth loss.

While plaque accumulations around the necks of teeth and subgingivally in the pockets of teeth may not be the only causative factors in decreased gum/tooth attachment and bone loss, the presence of such accumulations appears to be a necessary precursor for certain types of periodontal diseases, especially chronic adult periodontitis. If plaque is not removed, the microbiologic flora changes in character as it matures from predominately gram-positive to gram-negative. Gram-negative organisms have, as components of their cell walls, lipopolysaccharide molecules which have antigenic properties in humans. These lipopolysaccharide molecules, or fragments thereof, are also known as endotoxins because of their highly toxic properties in man. The endotoxins of many gram-negative bacteria associated with periodontal diseases, for example Bacteroides gingivalis, Actinobacillus actinomycetemcomitans, Bacteroides forsythus, Bacteroides intermedius and others have been shown to have antigenic and toxic properties in man.

Bacterial plaque may harden together with other calcific accretions to form calculus. This is made possible by high concentrations of calcium and phosphate in saliva. Thus, calculus is comprised of calcified necrosed bacteria and other calcific deposits. Calculus bound to the tooth represents a mechanical irritant. Because microbial plaque and plaque debris including endotoxin may be occluded within or bound to the calculus, calculus may also represent a toxic material with antigenic character.

Therapeutic treatment of periodontal disease ideally requires complete mechanical removal of calculus and infecting bacteria and their residues, including endotoxin bound to or occluded within plaque and calculus. Hand-scaling is slow and laborious, but offers tactile feedback to the skilled hands of the practitioner; whereas high speed scaling, wherein the vibration of a mechanically assisted scaler is generally above 10,000 cycles per second, provides for removal of calculus and reduces the effort required by the dental practitioner at the expense of tactile feedback. High speed devices and their uses are extensively documented in the literature.

An objective of the present invention is to provide irrigants which may be employed together with prior art instruments for scaling and root planing and to debride the teeth of calculus in order to augment and enhance the effectiveness of these techniques in removing and thereby mitigating the effects of irritating, toxic and antigenic effects of calculus, plaque and plaque debris, including endotoxin. A further objective is to remove sources of chronic inflammation and irritation and to cleanse the gingival sulcus of toxin laden calculus, plaque and plaque debris.

PRIOR ART DEVICES

It is known in the art to deliver antimicrobial solutions as a lavage to the sulcus or pocket affected by periodontal disease using commercially available delivery devices. An example is the Water Pik™. Such prior art devices comprise a variety of configurations to deliver lavage solutions but are not used to scale and mechanically debride teeth. Rather their benefit resides in the delivery and lavage of the antimicrobial solutions, presumably to kill plaque microorganisms and to rinse away soft, loosely adhered plaque. Generally, the irrigants chosen for use in the prior art devices are those that are available as mouthrinses with antimicrobial activity. They comprise a medicament and a vehicle or carrier. Examples of medicaments are sanguinarine, chlorhexidine, cetyl pyridinium chloride, zinc chloride, substituted phenols and the like. The selection of ingredients other than the medicaments is based generally on flavor perception and the need for stabilization of the solutions. The vehicle most frequently used comprises water and ethanol or a polyol and a surfactant as a means to keep otherwise immiscible flavoring oils dissolved, solvated or dispersed in the solution. Coloring agents and sweeteners may be present. Examples of commercially available mouthwashes used for this purpose include Listerine™, Listermint™, Scope™, Cepacol™, Peridex™ and Viadent™.

It is known in the art that plaque and calculus can be removed from teeth by mechanical scaling, especially at high frequency, including ultrasonic frequencies.

Copending application, U.S. Ser. No. 141,355, filed Jan. 6, 1988, assigned to Dentsply International Inc. incorporated herein by reference, now abandoned, discloses a delivery device for delivery of multiple irrigants to an infected site through the apex of a hollow ultrasonic scaler, to provide for simultaneous delivery of one or more irrigants and debridement while scaling the tooth. The device is intended especially for subgingival scaling, root planing and debridement at ultrasonic speeds.

Ultrasonic scalers vibrate at speeds greater than about 20,000 cps. Additionally, it is known in the art to use mechanical scalers that vibrate at lower speeds, greater than about 100 cps but less than 20,000 cps, which are known as sonic scalers. It is most common to use water as the irrigant in commercially available prior art sonic and ultrasonic scalers.

OBJECTIVES OF THE INVENTION

An objective of the invention is to provide irrigant solutions that are operative in all modes and methods of scaling but are especially valuable in sonic and ultrasonic high speed, mechanically assisted scaling methods wherein the irrigant is simultaneously delivered subgingivally to make it continuously available.

A further objective of the invention is to make available irrigants that chemically assist in the removal of plaque, plaque debris and calculus from the tooth and by doing so cleanse the tooth and pocket of antigenic and mechanically irritating deposits which are sources of chronic irritation and inflammation.

A further objective is to provide irrigants that are better able to cleanse the tooth and periodontal pockets to provide surfaces that favor epithelial reattachment between soft tissue and the tooth by producing a clean tooth surface free of calculus, microbial plaque and plaque debris and residues, especially endotoxin.

Another objective is to provide irrigating solutions that are useful in treating periodontally diseased pockets of teeth -to cleanse the tooth of calculus, bacterial plaque and plaque debris including endotoxin, and thereby reduce chronic inflammation.

Another objective is to provide irrigants affording the above advantages while simultaneously providing the adjunctive benefits of medicaments which may be added as supplementary components. These may include antiseptics, anti-microbials, astringents, anesthetics, antibiotics, anti-inflammatories, fluorides, enzyme inhibitors, monoclonal antibodies and the like, whether free in solution or contained within vesicles such as within liposomes.

SUMMARY OF THE INVENTION

The dental treatment material of the invention comprises one or more surfactants of the type that can solvate plaque and endotoxin, and preferably one or more calcium chelating agents to aid in removal and inactivation of solvated calculus, plaque and endotoxin. The dental treatment material is preferably used as an irrigant and is adapted to help dislodge, suspend, solvate, disperse, and/or emulsify microbial plaque, plaque debris, residues and constituents including endotoxins, and stain and calculus which may be found attached to the tooth. Examples of surfactants which are preferred in the irrigant include the ionic surfactants, a preferred one being sodium lauryl sulfate.

Irrigants containing surfactants alone do not have the efficiency required to remove and solvate infected calculus as efficiently under actual conditions of use as those of the present invention containing calcium chelating agents. It has been found that chelating agents soften and otherwise assist in the removal of calculus adhered to teeth In addition, it has been found that the addition of calcium chelating agents to surfactant solutions augments the removal of endotoxin.

Chelating agents of the invention are chosen from those which are effective calcium chelators, for example citric and ascorbic acids, ethylene diamine tetraacetic acids, their analogs and their salts. Ethylene diamine tetraacetic acid and its analogs including salts thereof are preferred and most preferred are the sodium salts of ethylene diamine tetraacetic acid and its analogs.

It is desirable, in the formulation of the irrigant of the invention, to avoid a composition that causes excessive salvation of tooth enamel. Etched enamel surfaces should not be a consequence of the method and composition of the invention.

Surfactant(s) and chelating agent(s) are formulated with vehicles chosen to appropriately solvate or disperse all the formulation ingredients and provide a stable free-flowing liquid physiologically acceptable oral composition. A free-flowing liquid is defined as one that can be delivered subgingivally through a mechanical device without clogging the device. Commercially acceptable irrigants are most often required to have a taste derived from essential oils and flavor in order to mask the otherwise normally unacceptable taste of the compositions, and therefore it is preferred in the usual instance to include up to about 30% by weight of ethanol and a solubilizing surfactant, an example of which is polyoxyethylene (20) sorbitan monooleate (Polysorbate 80). Preferred contents of taste enhancers such as flavoring oils and sweeteners is 0.001 to 3% by weight of the irrigant, more preferably 0.01 to 2%. In the usual instance coloring dyes are also preferably included. The irrigant preferably has a water content of 75 to 99% and in some preferred instances, especially when alcohol is included 80 to 95%.

In certain species of the invention, the viscosity of the composition may be increased significantly to enhance its utility in procedures used to debride the tooth of calculus and endotoxin. Viscosity control in this case is established by the addition of 0.1 to 10% by weight of a gelling or thickening agent, an example of which is hydroxyethyl cellulose. Other species of the invention include medicaments intended to achieve additional and specific purposes Medicaments used may include antiseptics, anti-microbials, astringents, anesthetics, antibiotics, anti-inflammatories, fluorides, enzyme inhibitors, and monoclonal antibiodies, which can be free in solution or may be carried in solution, for example, within liposomes.

DETAILED DESCRIPTION OF THE INVENTION

The dental treatment material of the invention may be applied by swabing on or in other ways but is preferably an irrigant/lavage composition used with scaling technique especially subgingivally in dental devices suitable for simultaneous scaling and irrigation of the tooth and gingival crevice or pocket. The irrigant/lavage compositions of the invention are particularly adapted for use in sonic and ultrasonic scaling apparatus and especially in equipment such as that sold by Dentsply International Inc. under the brand name CaviMed™ for ultrasonic scaling with supply of the fluid through a small diameter scaling tip into the periodontal pocket. The scaling tip has a passage way on the order of 0.009 inch in diameter. The composition of the invention is formulated, by the use of surfactants and calcium chelating agents, to chemically assist in the removal of plaque, plaque debris and calculus during the scaling procedure. In addition, the irrigants of the invention in some preferred species include medicaments that provide antiseptic, anti-microbial, astringent, anesthetic, antibiotic, and anti-inflammatory properties. The preferred anti-inflammatory medicaments in the usual instance are the non-steroidal types Also included may be fluorides and other anti-cariogenic agents, enzyme inhibitors, monoclonal antibodies and the like. The medicaments may be provided free in solution or may be contained within vehicles, such as within liposomes.

The irrigants of the invention contain one or more surfactants of the plaque and endotoxin solvating type and one or more calcium chelating agents in safe and effective amounts in an aqueous vehicle. The irrigant further contains 0–30% ethanol or non-toxic polyhydric compounds, which may be added as a means to aid in dissolving, solvating or dispersing some of the otherwise insoluble or poorly dispersible ingredients in the composition. Preferred alcohol contents are 5 to 20%, more preferably 7 to 15%, by weight based on the total weight of the composition. Ethanol is preferred.

Other suitable polyhydric alcohols will be apparent to those skilled in the art. Optionally, the irrigant may also contain viscosity control agents in the form of water soluble polymers such as hydroxyethyl cellulose, hydroxymethyl cellulose, hydroxypropyl cellulose, carboxymethyl cellulose and hydrolyzated starch, medicaments chosen for specific additional therapeutic purposes, taste enhancers such as flavors and sweeteners, and colorants.

It is important in choosing ingredients to be included in the irrigants of the present invention that they not interfere with operation of dispersing equipment and treatment. Such irrigants should be substantially free of polyols or other substances having significant humectant tendencies, and should be substantially or relatively non-foaming and relatively non-sticky.

An example of a viscosity control agent that is useful in certain preferred formulations is hydrogenated starch hydrolyzate which may serve as a partial replacement for polyhydric polyols as sweetener/flavor enhancing compounds and replacements for those commonly used, especially glycerin and sorbitol. The compounds produced are equally palatable and effective and yet are substantially non-sticky when allowed to dry on the hands. Hydrogenated starch hydrolyzate compounds are oligomers of sorbitol whose apparent sweetness covers a broad range from sweeter than to much less sweet than sorbitol. Similarly the higher oligomers have lesser humectancy decreasing with molecular weight, and are similarly less deliquescent, so that upon drying the residue of irrigants of the invention may be formulated to avoid residual stickiness and clogging tendency in the scaling/lavage apparatus. Compared to glycerin or sorbitol, the hydrogenated starch hydrolyzate used in the formulation of Examples 24 and 26 is found to be less sticky and of satisfactory character for use in such irrigants.

Surfactants that may be useful to solvate plaque and endotoxin include those having a molecular weight (MW) of 50 to 500, preferably 100–400, and most preferably 150–250. Exemplary of such surfactants are the salts of aromatic, aliphatic, or substituted aromatic or aliphatic carboxylic acids. As used herein, substituents may comprise lower aliphatic of 1–12 carbon atoms, phenyl, lower alkyl substituted aromatic of 6–15 carbons, amino, hydroxyl, carboxyl, halogen, lower alkyl ether, lower alkyl ester, amido, amino, oxido, carbonyl, and mixtures and salts thereof. As used herein, lower alkyl represents 1–12 carbon atoms unless otherwise specifically defined. Exemplary also of the salts that may be used are the sulfate salts, sulfonate salts, phosphate or phosphonic acid salts, preferably the ammonium, sodium, potassium or lithium salts of such acids, such as lithium or sodium lauryl sulfate. Other such surfactants are, block polyethers, for example the segmented block co(polyethylene oxide/polypropylene oxide) polymers, for example those produced commercially by the Wyandotte Division of BASF Inc.; polyoxyethylene alcohols, for example the commercial products sold by the Union Carbide Corporation under the tradename CARBOWAX and the like; substituted amino acids and other nonionic and ionic and quaternary compounds, examples of which include dodecyldimethylamine oxide, dioctosulfosuccinate sodium salt, cetylpyridinium chloride, chlorohexidine gluconate, N-lauryl imidoproprionic acid, N-lauryl sarcosinate, and the like.

The surfactants capable of solvating plaque and endotoxin are preferably employed at concentrations of between 0.01 and 5% by weight of the irrigant/lavage composition, more preferably between 0.05 and 1%, and most preferably between 0.25 and 0.75%. It has been found that excessively high concentrations of surfactant may not further enhance the removal of endotoxin while resulting in excessive and unnecessary foaming. The preferred surfactants of the plaque and endotoxin solvating type are the ionic surfactants and the more preferred are the alkali metal and ammonium alkyl salts and the most preferred are the alkali metal and ammonium alkyl salts of sulfate and sarcosinate, especially sodium alkyl sulfate. A readily available and preferred effective surfactant is found to be sodium lauryl sulfate. Sodium lauryl sulfate is widely used in tooth paste formulations for its foaming and cleansing ability of the supragingival tooth. Substantial foaming is undesirable during the preferred use of the treatment but as used in the present invention foaming is relatively low and does not obscure excessively the treatment site in the patient's mouth or oral cavity during the doctor's or clinician's treatment.

Additional dispersion surfactants may be optionally used which primarily aid in the dispersion of flavor oils and medicaments in the aqueous vehicle but may offer little contribution to salvation of endotoxin. Examples of such surfactants are polysorbates, examples of which are the esters of sorbitol and its anhydrides copolymerized with varying mole concentrations of ethylene oxide commercially identified for example as the Tween series produced by ICI Chemicals; polyether adducts, as typified by the aliphatic, aryl or mixed ethers of polyethylene oxide and its copolymers; and ester-ethers, typified by the aliphatic, aryl or mixed carboxylic acid esters of polyethyleneoxide and its copolymers or polyols, for example the commercial products known under the tradename SPAN produced by ICI America, Inc.

Examples of preferred calcium chelating agents include citric and ascorbic acids, and the more preferred ethylene diamine tetraacetic acid, and its analogs as exemplified by ethylene diamine diacetic acid, 1,2-Diaminocyclohexane-N, N,N',N'-tetraacetic acid, ethyleneglycol-bis(2 aminoethylether)-N,N'-tetraacetic acid and the like, and their salts, especially preferred are their alkali metal and ammonium salts, for example their lithium, ammonium, potassium, sodium and mixed salts. Particularly preferred is ethylene diamine tetraacetic acid disodium salt. It is widely used in foodstuffs as a preservative and chelating agent and has been found to be an especially effective ingredient in the present invention. Chelating agents are preferably employed at concentrations between 0.1 and 5% by weight, preferably between 0.25 and 3%, and most preferably between 0.4 and 1.5% by weight of the irrigant/lavage composition.

Examples of other commercially available chelating agents that may be used in the invention are L-ascorbic acid and its hemicalcium salt, dipotassium salt, disodium salt, or sodium salt; L+ ascorbic acid; L-ascorbic acid-2-sulfate; citric acid and its diammonium salt, trilithium salt hydrate, tripotassium salt, or trisodium salt dihydrate; ethylenediamine tetraacetic acid (EDTA) and its dipotassium, dilithium, disodium, tripotassium, tetrasodium, disodium-calcium, disodium-cuprous, sodium-ferric, disodium magnesium, diammonium or ammonium ferric salts. Other suitable chelating agents will be apparent to those skilled in the art.

It has been found that the use of the composition of the invention as an irrigant in conjunction with scaling procedures and as a lavage reduces chronic inflammation and improves the ability to rapidly cleanse a tooth to provide a surface that favors epithelial reattachment.

It has been found that a too high concentration of chelating agent dissolves tooth enamel, and that, in general, an increase of solvating agent beyond a particular concentration may diminish the effectiveness in removing endotoxin. It has been found in the present invention that in using a combination of a plaque/endotoxin solvating agent and a calcium chelating agent that effective calculus plaque and endotoxin removal can be obtained beyond that which can safely be achieved using either a solvating agent or chelating agent alone. Accordingly, in order to optimize the effectiveness of the irrigant of the invention, it is desirable to choose a surfactant and a chelating agent in combination that optimizes the dispersing, suspending, dissolving, and/or emulsifying of plaque and plaque debris including endotoxin and calculus.

A preferred pH would be acidic to very slightly alkaline, between 3 and 7.5, more preferably 4 and 7, most preferably 5.5 and 6.5. It is preferred that the irrigant have a slightly acid pH. The irrigant composition of the present invention needs to be stable for a period of time to enable distribution and storage. The preferred minimum stable period is at least 6 months, more preferably one year and most preferably for 2 years. During this time the ingredients should remain relatively active for their intended purposes when stored at usual ambient temperatures unrefrigerated. Thus when stored at from 60–80° F. the irrigant should remain a stable free-flowing physiologically acceptable oral composition that drys with a relatively non-sticky residue.

Specific compositions that have these properties, and the method by which they were achieved, are illustrated by the following examples.

It should be noted that the examples are illustrative only and should not be considered as limiting the invention.

EXAMPLE 1–11

An in-vitro method was used to determine the ability of various irrigant solutions to remove endotoxin using a limulus amoebocyte lysate assay. Aqueous irrigating solutions were prepared by preparing a carrier containing 10% by weight ethanol and 0.015% by weight of menthol as a flavor ingredient, and adding the following listed concentrations of polysorbate 80 (PS80), sodium lauryl sulfate (SLS), and ethylene diamine tetraacetic acid disodium salt (EDTA(Na)$_2$). The irrigating solutions were prepared by dissolving PS80 and menthol in the required amount of ethanol. Water was then added with stirring, and finally the SLS was dissolved in the aqueous solution.

To determine the efficiency of the solution in removing endotoxin, the following procedure was used. Microtiter wells of a polystyrene tray were inoculated with 100 ul of a preparation containing 50 Eu/ml (endotoxin units per milliliter) of *E. coli* 055:b5 endotoxin standard (Sigma Chemical), depositing a final quantity of 5 Eu/well, which was then allowed to dry overnight at room temperature. The microtiter plates were stored in the refrigerator until used. 200 ul of a test solution was added to each well, and covered with Parafilm. A vibrating probe of an ultrasonic scaling tip (Model 200 Cavi-Med manufactured by Dentsply International Inc.) was inserted into each well through the Parafilm to agitate the test solution in the well. The solution was agitated in this manner for 30 seconds without touching the walls of the well. The test solution was then removed with a non-pyrogenic pipette, and placed in a non-pyrogenic 10×75 mm culture tube. The test solution was diluted with non-pyrogenated sterile water in sequential 1:1 dilutions to provide 1:1, 1:2, 1:4, 1:8 dilutions of solution from each test well. 100 ul of each of the four dilutions were placed in test tubes.

A set of endotoxin references was prepared with 5 concentrations (a series of 1:1 dilutions) ranging from 0.0625–1.0 Eu/ml endotoxin. A negative control was prepared using non-pyrogenic sterile water. A solution containing limulus amoebocyte lysate (IAL) from Cape Cod Associates was prepared by adding 5.2 ml non-pyrogenic sterile water with mild shaking. 100 ul of prepared LAL solution was added to each of the test tubes and incubated in a water bath at 37° C. for one hour without disturbing the tubes. The test was evaluated by gently inverting the tube. A solid gel was indicative of a positive reaction. The test solutions were prepared and the tests repeated five times for each solution to evaluate the percent of endotoxin removed.

The results of the experiments are shown in Table 1. The results show that EDTA and SLS in combination enhance the effect in the removal of endotoxin. The data show that the carrier, comprised of an alcohol-water solution, has substantially no effect in removing endotoxin.

In the table, the carrier comprises a 10% by weight ethanol in an aqueous solution. The amount of each the ingredients used is described in percent by weight based on the total weight of the solution PS80 represents polysorbate 80, which is known specifically as polyoxyethylene sorbitan monooleate. All ingredients are represented in percent by weight.

TABLE 1

| | EXAMPLE | | | | | | | | | | |
|---|---|---|---|---|---|---|---|---|---|---|---|
| | 1 | 2 | 3 | 4 | 5 | 6 | 7 | 8 | 9 | 10 | 11 |
| PS80 | 0.15 | 0.15 | 0.30 | 0.30 | 0.15 | 0.15 | 0.30 | 0.30 | 0 | 0.30 | 0 |
| SLS | 0.13 | 0.13 | 0.13 | 0.13 | 0.25 | 0.25 | 0.25 | 0.25 | 0 | 0 | 0 |
| EDTA (Na)$_2$ | 0 | 0.75 | 0 | 0.75 | 0 | 0.75 | 0 | 0.75 | 0.75 | 0.75 | 0 |
| % ENDOTOXIN REMOVED FROM PLASTIC MICROTITER WELLS | | | | | | | | | | | |
| % | 33 | 42 | 25 | 30 | 20 | 30 | 20 | 33 | 17 | 8 | 0 |

The data illustrates that an optimal tested amount of PS80 in the illustrated and exemplary composition is about 0.15% by weight. (Compare Examples 2 and 4). Also, about 0.13% by weight SLS is an optimal amount in the solution (compare Examples 3 and 6). Furthermore, the addition of EDTA(Na)$_2$ to the solution optimizes the removal of endotoxin. (Compare the odd numbered Examples with the even numbered Examples.)

EXAMPLE 12–17

Another test procedure was used to show the effectiveness of irrigants of the invention against endotoxin associated with known periodontal disease.

To carry out the test procedure, cementum was harvested and pooled from a series of teeth that were extracted as a consequence of frank periodontal disease as a source of contaminated tissue. Endotoxin concentration was determined by an LAL chromogenic assay by exhaustive extraction of an aliquot of the pooled tissue with saturated citric acid solution. Other aliquots of the pooled sample were treated with each of the test solutions described in Table 2. The percent reduction in endotoxin value of each aliquot was assayed and reported in Table 2. Concentrations of ingredients is in parts by weight. The solutions were made as described in Examples 1–11.

TABLE 2

| | EXAMPLE | | | | | |
|---|---|---|---|---|---|---|
| | 12 | 13 | 14 | 15 | 16 | 17 |
| PS80 | 0.15 | 0.15 | 0 | 0.15 | 0.15 | water |
| SLS | 0.13 | 0.38 | 0 | 0.13 | 0.13 | control |
| EDTA (Na)$_2$ | 0.75 | 0.75 | 0 | 0.15 | 0 | * |
| NaHCO3 | 0 | 0 | 0 | 0.11 | 0 | * |
| Sodium Citrate | 0 | 0 | 0 | 0 | 0.38 | * |
| Citric acid | 0 | 0 | 0 | 0 | 0.38 | * |
| % ENDOTOXIN REDUCTION IN INFECTED CEMENTUM AFTER TREATMENT | | | | | | |
| Static | 79 | 55 | 15 | 85 | 87 | 2 |

The tests were each repeated 5 times except for Example 12 which was repeated four times.

The solutions were formulated with a carrier comprised of 10 parts by weight (pbw) alcohol SD38B, 90 pbw deionized water, 0.01 pbw aspartame sweetener, and flavor. Non-pyrogenic sterile water (Example 17) was a control. Carrier without flavor (Example 14) was an internal control. Solutions were identified by code number and tests were conducted by technicians without knowledge of the compositions used.

The irrigant used in Example 12 is similar to test Example 2, except for the addition of additional flavor and colorant. Example 13, was prepared with an increased concentration of SLS. Results show a lower efficiency in endotoxin removal for Example 13 compared to the irrigant of Example 12, a result that parallels the effect observed by increasing the concentration of SLS in Example 4 compared to that of Example 2.

The use of non-pyrogenic sterile water was found to have little value in removing endotoxin in the study. Water is the most widely used irrigant in high speed scaling apparatus. Likewise, the internal blind control comprised of alcohol and water proved to be of little value in the removal of endotoxin.

Partial neutralization of ethylene diamine tetraacetic acid disodium salt by the addition of sodium bicarbonate (Example 15) has been shown to enhance endotoxin removal. It was expected that this form of the solution would have greater capacity to rapidly chelate calcific deposits, but it was not anticipated that endotoxin removal would be enhanced The value of such a solution lies in its enhanced calcium chelating abilities which are reflected in more rapid removal of calculus, plaque and stain from teeth while simultaneously providing for enhanced removal of endotoxin.

In general, the data obtained in Examples 1–17 show that, in the illustrated embodiment, optimal results were obtained using compositions comprising by weight: about 0.08–0.30% PS80, 0.08–0.25% SLS and 0.35–1.50% EDTA (Na)$_2$ and 0–0.25% sodium bicarbonate in an aqueous vehicle comprising about 5–15% by weight ethanol; and about 0.08–0.30% PS80, 0.08–0.25% SLS, 0.20–0.75% sodium citrate, 0.20–0.75% citric acid in an aqueous carrier comprising about 5–15% by weight ethanol.

EXAMPLE 18

This example provides a measure of the in-vivo efficacy of selected solutions of exemplary compositions of the invention described in earlier examples, compared to water or a commercially available prior art irrigant. From the viewpoint of the practitioner, who is limited in time to achieve an essential objective, the ability to quickly and effectively debride the tooth and remove stains and calculus is most essential. Calcified deposits are well adhered to the tooth and frequently hard to remove. In order to measure these characteristics the solutions of Examples 12, 15, 17 (distilled water) and a commercial irrigant, ProSol™ CHX, containing 0.12% chlorhexidine and polysorbate 80 (1.00% by weight) in an alcoholic (11.6%) aqueous solution, were compared in a clinical setting where the teeth of dogs were debrided and cleaned of calculus and stain in a blind study with respect to the solutions used. Three operators made separate evaluations. In all cases the solutions of Example 15 were determined to be most effective in removing plaque and calculus, and the solution of Example 12 was a close second in efficacy. The dogs showed normal recovery following the scaling without evidence of irritation.

In order to assure that the representative solution of Example 15 did not remove enamel to any significant extent, scanning electron micrographs were prepared of extracted teeth scaled ultrasonically using the Cavi Med scaling unit (a product of Dentsply International Inc.) dispensing the solution of Example 15 for 1 minute and then stored in the solution of Example 15 for 9 minutes each. The teeth were viewed at a magnification of 1000 times. No deleterious effects were noted in the enamel. Surfaces of cementum were cleaned of the usual layer of amorphous material (smear layer) normally found on cementum. This physical effect confirms the utility of these solutions in providing rapid and effective removal of calculus, plaque and plaque debris from teeth.

EXAMPLES 19–29

Eleven aqueous dental treatment solutions were prepared as described in Table 3. The materials were added under conditions of stirring.

TABLE 3

| | EXAMPLE | | | | | | | | | |
|---|---|---|---|---|---|---|---|---|---|---|
| | 19 | 20 | 21 | 22 | 23 | 24 | 25 | 26 | 27 | 28 |
| PS80 | 0.15 | 0.15 | — | 0.15 | 0.15 | 1.0 | — | 0.5 | — | 1.0 |
| FLAVOR | 0.05 | 0.05 | — | 0.05 | 0.05 | 0.2 | — | 0.05* | — | 0.2 |
| ALCOHOL | 10.00 | 10.00 | 10.00 | 10.00 | 10.00 | 11.59 | — | 10.00 | — | 11.6 |
| WATER | 90.00 | 90.00 | 90.00 | 90.00 | 90.00 | 84.49 | 100.00 | 87.36 | 100.0 | 84.5 |
| SWEETNER | 0.01 | 0.01 | 0.01 | 0.01 | 0.01 | 0.04 | — | 0.05 | — | 0.0 |
| H. STARCH | — | — | — | — | — | 2.00 | — | 2.0 | — | 2.0 |
| EDTA-Na$_2$ | 0.75 | 0.75 | — | 0.75 | — | — | — | — | — | 0.75 |

TABLE 3-continued

| | EXAMPLE | | | | | | | | | |
|---|---|---|---|---|---|---|---|---|---|---|
| | 19 | 20 | 21 | 22 | 23 | 24 | 25 | 26 | 27 | 28 |
| CHX | — | — | — | — | — | 0.689 | — | — | — | — |
| SLS | 0.125 | 0.375 | — | 0.125 | 0.125 | — | — | — | — | — |
| SLSa | — | — | — | — | — | — | — | — | 2.0 | — |
| NaHCO3 | — | — | — | 0.11 | — | — | — | — | — | — |
| Na Citrate | — | — | — | — | 0.375 | — | — | — | — | — |
| CITRIC ACID | — | — | — | — | 0.375 | — | — | — | — | 0.0006 |
| B ACID | — | — | — | — | — | — | — | 0.0001 | — | — |
| GREEN 3 | — | — | — | — | — | — | — | 0.000025 | — | — |
| GREEN 10 | — | 0.0001 | — | 0.000025 | — | — | — | — | — | — |
| YELLOW 6 | — | — | — | — | — | 0.00055 | — | — | — | — |
| YELLOW 10 | — | — | — | 0.00025 | — | — | — | 0.00025 | — | 0.0005 |
| RED 33 | 0.00005 | 0.00002 | — | — | 0.00005 | — | — | — | — | — |
| CPCl | — | — | — | — | — | — | — | 0.045 | — | — |
| ZCl | — | — | — | — | — | — | — | — | — | 0.2 |

Quantities are percent by weight. Weighing tolerances: +/− 0.01%
Materials are added in the above order, dissolving each in the prior addition before adding the next.
PS80 is polysorbate 80 (Tween 80, NF grade from Serva Feinbiochemica)
FLAVOR is peppermint flavoring oil (Ungerer Flavor 16390)
FLAVOR* is raspberry mint #59 190/A
ALCOHOL is denatured ethanol (SD Alcohol 38B from AAPER Alcohol and Chemical Company, Shelbyville, Kentucky)
WATER is deionized water filtered through a bacteria filter
SWEETENER is Aspartame (Nutrasweet)
H. STARCH is hydrogenated starch hydrolysate (Hystar 5875)
EDTA is ethylene diamine tetraacetic acid disodium salt (crystal CAS Reg. 6381-92-6 from Fisher Scientific)
CHX is chlorhexidine gluconate (Spectradyne G. from Lonza)
SLS is Sodium Lauryl Sulfate (NF grade from Fisher Scientific)
SLSa is Sodium Laural Sarcosine (Sigma Chemical Co.)
NaHCO3 is Sodium bicarbonate (USP grade from Fisher Scientific)
Na CITRATE is sodium citrate Na C-0909 (Sigma Chemical Co.)
CITRIC ACID
B ACID is Benzoic acid
GREEN 3 is D & C green #3
GREEN 10 is D & C green #10
YELLOW 6 is D & C yellow #6
YELLOW 10 is D & C yellow #10
RED 33 is D & C red #33
CPCl is Cetyl pyridinium Chloride
ZCl is Zinc chloride
ANTI is the antibiotic polymixin B (Sulfate from Serva Feinbiochemica)

The pH of Example 19 was 4.6, the pH of Example 22 was 6.5 and the pH of Example 24 was 4.5 with the pH measurements being to an accuracy of ±0.5.

The solutions of Examples 19–29 were tested for extraction of endotoxin by the following procedure with the results given in Tables 4, 5, 6 and 7.

TESTING

Materials and Methods

Preparation of Materials

Throughout this study all glassware, burs, curettes and other heat resistant materials were made pyrogen-free by heating 180° C. for four hours. Sterile, pyrogen-free water was obtained commercially (Kendall McGaw Labs., Inc., Irvine, Calif.) All solutions were prepared in pyrogen-free water using pyrogen-free glassware. All plastic products used were new and sterile.

Preparation of Root Material Pool

Root surface material was collected from single and maturated teeth which were extracted following a clinical diagnosis of CIPD and also satisfying the following criteria: (1) radiographic evidence of at least 30% bone loss; (2) no history of scaling or root planning in 12 months or periodontal surgery in the past twenty-four months; (3) no root surface or coronal caries or restorations located subgingivally; (4) no antibiotic therapy during the previous month.

Prior to extraction, supragingival accretions were removed with a curette and the level of the gingival margin was clearly marked with a sharp pencil or dental bur. Following extraction, adherent blood was washed away with a stream of pyrogen-free water and each tooth was placed in a test tube and stored at −10° C. until used.

Processing of the periodontally involved teeth was essentially as described by Wilson et al (1986). Prior to processing, each tooth was thawed in its container and its root surface gently agitated in 20 ml of pyrogen-free water to remove any loosely adherent material. The tooth was then dried on pyrogen-free aluminum foil and placed in a desiccator (Silica Gel Desiccant) at room temperature. Visible subgingival calculus was then removed with Columbia #13/14 curettes and pooled. Shallow circumferential grooves were cut with a straight #35 inverted bur to a depth of 1 mm immediately apical to the gingival margin and coronal to the readily identified most coronal remnants of periodontal ligament. These two grooves were then connected with straight #57 fissure burs in a slow moving handpiece. Root shavings from 200 teeth were pooled, ground in a mortar, and passed through a 90 µm pore size sieve.

Preparation of Calculus Pool

The subgingival calculus removed from the teeth described above was pooled with supra and subgingival calculus harvested from the teeth of an additional 250 teeth.

The additional teeth necessary to obtain sufficient calculus for the study did not necessarily meet the criteria used for the teeth in the root material pool. The pooled calculus was ground to uniformity with a mortar and pestle but was not sieved and stored at −10° C.

Extraction of Endotoxin

Endotoxin was extracted from treated and untreated root material and calculus using 1.0 M citric acid with a procedure based on that described by Fine et al (1980). A 20 mg sample of root material was extracted with 1.0 ml citric acid for 10 min at 37° C. During the incubation period the sample was vortexed vigorously for 30 sec. The sample was centrifuged at 3000 rpm for 15 min, followed by the removal of the supernate to a clean tube. The pellet was washed with 1.0 ml of water and recentrifuged (3000 rpm, 15 min.) The supernate from the wash was combined with the original supernate giving 2.0 ml of extract containing endotoxin. To remove the citric acid, each extract was concentrated with a Centricon 30 microconcentrator (Amicon, Danbers, Mass.). The recanted (0.1 to 0.2 ml) was reconstituted to 1.0 ml with Tris buffer (0.1 M pH 7.5). The same extraction procedure was used with the calculus samples except that the sample size was reduced to 5.0 mg.

Treatment of Samples with Test Solutions

Eleven test solutions were supplied by Dentsply International (York, Pa.). At the time the solutions were tested, their chemical composition was known only to the supplier.

1. Static Treatment

One ml of test solution or water was added to 5 replicate samples of root material (20 mg) or calculus (5 mg) and mixed on a Vortex mixer. The solutions were incubated for 2 min. at 37° C., mixed again, and centrifuged at 3000 rpm for 15 min. The supernates were discarded and the pellets washed once with 1.0 ml water to remove residual solution. The washed pellets were then extracted with citric acid and analyzed for their endotoxin content.

2. Sonic Treatment

Root material was also treated with test solutions using ultrasonics. One ml of test solution was added to 5 replicate 20 mg samples of root material and treated with a Cavi-Med ultrasonic instrument (Dentsply International Inc., York, Pa.) for 2 min. at room temperature. Each vial of the 5 replicates was centrifuged (3000 rpm, 15 min.) immediately after treatment and supernate discarded. The pellets were then washed once with water, the pellets extracted with citric acid and the extracts assayed for their endotoxin content.

Endotoxin Assay

For the determination of endotoxin content of the extracts the quantitative chromogenic limulus amoebocyte lysate (LAL) assay (QCL1000, Wittaker Bioproducts, Walkerville, Md.) was used. The assay was performed according to the directions of the manufacturer. The endotoxin content of the root material and calculus samples with and without treatment with a solution was calculated using a computer program written for this purpose. Endotoxin values were calculated as Endotoxin Units (EU)/ml and as ng/ml of sample

RESULTS

The mean endotoxin content of the root material before treatment with test solutions was 6.34 ng/ml (0.132 ng/mg) and that of the calculus was 13.21 ng/ml (2.64 ng/mg).

Static elution of endotoxin from the root material by 11 test solutions and water was determined (Table 3). The solutions which removed the largest amounts of endotoxin from the root material were Examples 26 (89%), 23 (87%), and 22 (85%). Statistical analysis using a paired t test revealed that these solutions were significantly different ($p<0.05$) from Example 20 which gave a 55% endotoxin reduction. Comparing water to the untreated material revealed that water did not elute endotoxin from the root surface ($p>0.05$). The solution of Example 21 was also shown to be ineffective.

Solutions of Examples 25 and 27 require further comment. The results with Example 25 are higher in all 5 replicates than base-line endotoxin content of the root material suggesting contamination with extraneous endotoxin. In addition, this solution also gave high results in the sonic experiments (Table 5). This suggested that the solution of Example 25 itself contains LAL reactive material.

The solution of Example 27 presented a different problem which was not encountered elsewhere. After citric acid extraction, the root material did not pellet satisfactorily even when centrifuged at high speeds. Some of the material pelleted leaving a distinctly cloudy suspension and a pellicle. Further studies of this solution showed that a cloudy suspension with a distinct pellicle was produced when the solution was mixed 1:1 with 1M citric acid. The problem seemed to be due to residual solution on the root material after washing. Increasing the number of water washes to three did not remove this residual material. Therefore the results with this solution are not shown in Table 5.

The results of ultrasonic treatment of root material with 7 test solutions and water are shown in Table 5. Of the solutions tested the solution of Example 23 (94%) was the most effective in removing endotoxin followed by Examples 24 and 22. There were, in general only slight increases in endotoxin removal over static elutions when the solutions were applied to the root material using ultrasonics. In fact, the solution of Example 26 performed better with static elution. As with the static studies, water eluted very little endotoxin from the root material.

The solution of Example 21 was the carrier vehicle used in the other solutions without an active ingredient. The carrier vehicle only eluted up to 30% of the endotoxin under sonic conditions but was much less active than the other solutions.

Since ultrasonics did not greatly increase endotoxin elution tested in this manner, calculus samples were tested by static elution only. Six solutions and water were used with calculus samples. The results of this study are shown in Table 6. The solutions of Examples 19, 22 and 23 were very effective in eluting endotoxin from calculus. Each of these solutions removed over 90% of the endotoxin from the calculus extracts and performed better with the calculus samples than with root material (Table 7). The carrier vehicle and water performed better with calculus than with root material and the solution of Example 24 was less effective in this static elution of calculus than when used with infected cementum.

DISCUSSION

The amount of endotoxin (0.32 ng/mg) on the periodontitis affected teeth averaged out to 14.4 ng/tooth. This is greater than the 2.9 and 3.68 ng/tooth reported by Jones & O'leary (1978) and Nishimine & O'leary (1979) and less than $4.13 \times 10^3$ ng/tooth as noted by Wilson et al (1986). These differences are not surprising when one considers differences in assay systems as well as the preparation and processing of the teeth.

The differences seen in the ability of the test solutions to remove endotoxin from root material and from calculus samples is thought to be due to differences in the materials themselves particularly in their consistency. Sample size may also have played a role since there was a greater ratio of eluant to sample in the calculus specimens. Even with these differences, most of the solutions behaved similarly with the different samples and with the different types of t treatment (static vs. sonic).

A greater problem was seen with variation between replicate samples. This difficulty was encountered with both root material and calculus samples throughout the study. The complete protocol for treatment of the samples was long and complex and offered many points at which variation in replicate samples might occur. Despite attempts to control and standardize each step of the procedure, the variations which we found are thought to be due to the extensive treatment and extraction procedure. In the case of the calculus samples, the samples may not have been completely uniform since they were ground but not sieved to homogeneity.

A number of studies (Maidwell-Smith et al 1987, Wilson et al 1986) in addition to this one, have shown that endotoxin is present on periodontally diseased root surfaces though the amounts of endotoxin found have varied widely. Since these bacterial lipopolysaccharides are thought to play a role in the pathogenesis of periodontal disease, their removal during therapy should permit better reattachment to the root surface. In this study we have shown that several chemical solutions are able to remove LAL reactive material from both root surface material and calculus. The most effective solutions tested were those of Examples 23, 22, 26, 24, 19 followed by 20. The use of such chemicals as an adjunct to root planing should be useful in the treatment of periodontal disease. The solution of Example 21 was the least effective.

One of the problems, however of using such chemicals as mouth rinses, is the inability of these solutions to gain access to the base of the pocket. A new ultrasonic device has recently been marketed that combines a local delivery approach of medicaments with ultrasonic action. This is the device sold under the brand name Cavi-Med by Dentsply International Inc. and is the subject of U.S. patent application Ser. No. 141,355 earlier referred to in this application.

Chemical agents can be applied in a static mode or combined with ultrasonic activity. Daily et al (1982 Histological assessment of periodontally involved cementum, Journal of Clinical Periodontally 9,266-274D) have shown that bacterial products may penetrate to a depth of about 10 um and be present in resorption lacunae or as subsurface microbial contamination.

A topical delivery approach with solutions of the invention has been shown to reduce levels of endotoxins on periodontitis affected roots.

TABLE 4

Static elution of endotoxin from root material

| Example | No. Replicate Samples | Endotoxin (ng/ml) Mean S.D. | Range | % Reduction |
|---|---|---|---|---|
| Untreated | 5 | 6.34 + 0.934 | 5.02–7.5 | — |
| 19 | 4 | 1.34 + 0.230 | 1.04–1.57 | 79 |
| 20 | 5 | 2.90 + 0.739 | 2.0–3.77 | 55 |
| 21 | 5 | 5.41 + 0.429 | 5.0–5.89 | 15 |
| 22 | 5 | 0.94 + 0.216 | 0.66–1.24 | 85 |
| 23 | 5 | 0.85 + 0.205 | 0.58–1.13 | 87 |
| 24 | 5 | 1.29 + 0.181 | 1.08–1.53 | 80 |
| 25 | 5 | 9.57 + 0.867 | 8.72–10.98 | none |
| 26 | 3 | 0.70 + 0.042 | 0.64–0.78 | 89 |

TABLE 4-continued

Static elution of endotoxin from root material

| Example | No. Replicate Samples | Endotoxin (ng/ml) Mean S.D. | Range | % Reduction |
|---|---|---|---|---|
| 27 | 5 | —a | — | — |
| 28 | 5 | 1.34 + 0.386 | 0.91–1.75 | 81 |
| Water | 5 | 6.24 + 0.934 | 5.07–7.76 | 2 | a—Results not recorded due to precipitation of solution during analysis with citric acid.

TABLE 5

Ultrasonic elution of endotoxin from root material

| Example | No. Replicate Samples | Endotoxin (ng/ml) Mean S.D. | Range | % Reduction |
|---|---|---|---|---|
| Untreated | 5 | 6.34 + 0.934 | 5.02–7.5 | — |
| 19 | 5 | 1.53 + 0.916 | 0.63–2.99 | 76 |
| 21 | 4 | 4.42 + 0.486 | 3.75–4.82 | 30 |
| 22 | 5 | 1.02 + 0.248 | 0.67–1.27 | 84 |
| 23 | 4 | 0.36 + 0.059 | 0.28–0.41 | 94 |
| 24 | 5 | 0.87 + 0.105 | 0.78–1.04 | 86 |
| 25 | 5 | 7.17 + 1.038 | 6.07–8.42 | none |
| 26 | 5 | 2.24 + 0.733 | 1.31–3.15 | 65 |
| Water | 5 | 6.09 + 1.77 | 4.29–7.86 | 4 |

TABLE 6

Static elution of endotoxin from calculus

| Example | No. Replicate Samples | Endotoxin (ng/ml) Mean S.D. | Range | % Reduction |
|---|---|---|---|---|
| Untreated | 5 | 13.21 + 1.205 | 11.21–14.06 | — |
| 19 | 5 | 1.13 + 0.254 | 0.81–1.44 | 91 |
| 21 | 5 | 7.50 + 1.481 | 6.32–9.58 | 43 |
| 22 | 4 | 1.06 + 0.145 | 0.85–1.17 | 92 |
| 23 | 5 | 1.12 + 0.305 | 0.77–1.53 | 92 |
| 24 | 4 | 7.56 + 2.872 | 4.08–10.83 | 43 |
| 27 | 5 | 3.05 + 0.569 | 2.35–3.73 | 77 |
| Water | 5 | 5.04 + 1.730 | 3.2–7.77 | 62 |

TABLE 7

Comparison of static elution of endotoxin from root material and calculus

| Example | % Reduction of Root Material | Endotoxin in Calculus |
|---|---|---|
| 19 | 79 | 91 |
| 21 | 15 | 43 |
| 22 | 85 | 92 |
| 23 | 87 | 92 |
| 24 | 80 | 43 |
| 27 | — | 77 |
| Water | 2 | 62 |

EXAMPLE 29

The formulation of Example 22 was repeated except that Green 3 rather than Green 10 was used and it was visually evaluated that the color was improved.

The examples show a method which provides improved ability to debride calculus and stain from teeth in-vivo while simultaneously removing endotoxin from infected tooth root, by the preferred technique of ultrasonic scaling and irrigation. Significant reductions in the time required to achieve clinically satisfactory results have been shown in-vivo in animals. The compositions of irrigant are biologically compatible and good healing was demonstrated in animals so treated. Further, the examples have demonstrated that these results are achieved without harming the tooth by etching or dissolving or physiologically impairing tooth enamel. This may occur with excessively high concentrations of chelating substances such as concentrated citric acid.

The formulations of irrigant essentially contain appropriate surfactants which are themselves able to remove endotoxin from infected surfaces, and chelating agents with known ability to solvate inorganic tooth substance and calcified deposits, both of which are comprised of calcium phosphate compounds.

The examples have shown further that formulations of the invention are not optimally formulated except by consideration of the interactions between the constituent materials used at proper concentrations in the formulations and by methods described herein provided to achieve these purposes. Large or random concentrations of each essential component are problematic because they can cause excessive foaming and enamel dissolution and may not increase the ability to remove endotoxin, or may excessively etch the tooth.

The examples have described formulations which are effective in removing endotoxin from treated plastic microtiter wells and from excised infected human dentin and calcified deposits, both with and without ultrasonic activation. In clinical trials exemplary formulations have demonstrated the combined ability to reduce the time required to complete the laborious process of subgingival cleaning and debridement from the tooth of calculus and endotoxin, and to do so safely and effectively in a one-step operation in a manner superior to water or the presently available commercial representative irrigants containing for example chlorhexidine or zinc chloride. Cleaning the tooth of adhered, infected calculus, endotoxin and other bacterial products, which may have penetrated the surface layers of cementum and dentin subgingivally, is essential in superior treatment and prevention of periodontal diseases and in restoring a patient to good oral health.

It is an important feature of the present invention that a stable, free-flowing liquid physiologically acceptable oral composition be provided that can function reliably as an irrigant for use in scaling and/or lavage apparatus such as the apparatus sold under the tradename CaviMed by Dentsply International Inc. The oral composition of the present invention may, however, also be used by swabing on or as a mouthwash.

Solutions which have been prepared according to the invention may be thickened to form "gels" that can be applied directly to a tooth from a syringe, thus allowing greater control of their placement and longer residence times in situ, without the necessity for continuous irrigation. This mode of application is especially useful where the tooth is to be scaled with curettes and hand scalers, and where continuous flow of the unthickened solution from an integrally mechanical scaler of the type previously described, e.g. the CaviMed, is not employed.

Thus the "gel" or thickened solution of Example 30 was placed into the pocket of a tooth in-vivo which had tightly bound subgingival calculus deposits upon the tooth root. The "gel" was applied by means of a 3 ml syringe to which was attached a #25 side delivery irrigating needle (Maxi-Probe #24 gauge, MPL Inc., Chicago, Ill.) by means of a Luer-Lok attachment. The gel was allowed to remain in the pocket for 2 minutes after which time it was scaled with hand instruments. An adjacent tooth with similar calculus deposits was used as a control. The calculus was significantly more easily removed from the tooth pretreated with the "gel" or thickened solution. The calculus was softened and easily removed from the pretreated tooth as a dispersion within the gel, rather than upon fracture of the calculus from the tooth surface in large fragments as was the case with the untreated tooth. This finding was subsequently repeated using other teeth on this and other patients. The clinical information was provided by Dr. Robert Marrier, D.D.S. and Kyle Marrier, C.D.H.

In another mode of application, the "gel" or thickened solution of Example 30 was placed into a double sided foam tray of the type used to apply "fluoride" gels for 5 minutes. The patient applied pressure to the tray to hold it in place against the teeth, and the "gel" of Example 30 was forced between and around the teeth and subgingivally into the sulcus and pockets of teeth. After removal of the tray the teeth were scaled with hand instruments. The heavy calculus deposits supragingivally were softened and significantly more easily removed than similar deposits from patients without preconditioning using the gel. Additionally, subgingival residues were more easily removed where the gel had been forced subgingivally into sulci and pockets. The clinical information was provided by Dr. John Heyde, D.D.S. and B. Lehn, C.D.H.

While subjective in nature, these and other similar experiences are illustrative of the utility and application to which the solutions or "gels" may be applied with success.

EXAMPLE 30

A solution thickened to form a "gel" was obtained by preparing a composition comprising parts by weight:

| | |
|---|---|
| PS80 | 1.5 |
| FLAVOR | 0.5 |
| ALCOHOL | 100.0 |
| WATER | 882.0 |
| SWEETENER | 0.10 |
| EDTA-$Na_2$ | 7.5 |
| SLS | 1.25 |
| $NAHCO_3$ | 1.1 |
| GREEN 10 | 0.001 |
| GREEN 6 | 0.0009 |
| HEC | 1.8 |

HEC=Hydroxyethyl cellulose (Natrosol 250H, Aqualon Co., Wilmington, Del.)

Hyroxyethyl cellulose has been found to be useful for the solution thickening and at this time to be preferred for this application. It is clear, however, that other thickening materials providing similar results may be used, as for example, alginic acid salts and esters, locust bean gum, guar gum, gum tragacynth, carboxymethyl cellulose, polyvinyl acetate, polyvinyl pyrrolidone, aerogels of alumina and silica, and the like. These are illustrative only and not meant to imply they are the most suitable or the only products that may be used.

The "gel" of Example 30 had a viscosity of 38,000 cps determined using a Brookfiled Viscosimeter, Model LVT (spindle #4 @ 6 RPM), and a pH of 6.3. Higher or lower viscoisities may be used depending on the particular thickening material and the mode of application. In the case of hydroxyethyl cellulose concentrations from 0.1–10% are suitable, and concentrations form 0.2–4.0% are preferred, while concentrations from 0.3–3.0% are most preferred.

While present embodiments of the invention and methods of practicing the same have been illustrated and described, it will be recognized by those skilled in the art that the invention may be otherwise variously embodied and practiced within the scope of the following claims.

What is claimed is:

1. A method to remove calculus and endotoxin from a subgingival area of teeth in the oral cavity of a living animal comprising the steps of:
    applying from a syringe through a needle passage having a diameter on the order of 0.009 inch without clogging the passage to said area an oral gel composition comprising:
        an effective amount of water,
        from about 0.01 to about 5.0 percent by weight of a calculus and endotoxin solvating surfactant having a molecular weight of from about 150 to about 250,
        from about 0.1 to about 5.0 percent by weight calcium chelator, and
    scaling and debriding said area after said oral composition has been applied to said area for at least about 2 minutes, whereby calculus and endotoxin are removed from said area.

2. The method of claim 1 wherein said gel composition further comprises sodium bicarbonate.

3. The method of claim 1 wherein said gel composition further comprises an antimicrobial agent.

4. The method of claim 1 wherein said gel composition further comprises from about 0.1 to about 10 percent by weight of an agent effective to increase significantly the viscosity of said composition.

5. The method of claim 1 wherein said surfactant comprises from 0.05 to 0.75 percent by weight of said composition and said calcium chelator comprises from about 0.4 to about 1.5 percent by weight of said composition.

6. A method for scaling and debriding teeth in the oral cavity of a living animal to remove hard calculus from a subgingival area of said teeth comprising the steps of:
    softening said hard calculus by applying to said area, an oral gel composition comprising:
        an effective amount of water,
        from about 0.05 to about 1.0 percent by weight of a calculus solvating surfactant having a molecular weight of from about 100 to about 400,
        from about 0.4 to about 1.5 percent by weight calcium chelator, and
    scaling and debriding said softened calculus from said area with a scaling tip after said oral gel composition has been applied through a needle passage having a diameter on the order of 0.009 inch without clogging the passage to said area for at least about 2 minutes, whereby said softened calculus is removed from said area.

7. The method of claim 6 wherein said gel composition further comprises sodium bicarbonate.

8. The method of claim 6 wherein said gel composition further comprises an antimicrobial agent.

9. The method of claim 6 wherein said gel composition further comprises from about 0.1 to about 10 percent by weight of an agent effective to increase significantly the viscosity of said composition.

10. The method of claim 6 wherein said surfactant comprises from 0.05 to 0.75 percent by weight of said composition and said calcium chelator comprises from about 0.4 to about 1.5 percent by weight of said composition.

11. A method of using a viscous liquid for scaling and debriding to remove calculus and endotoxin from a subgingival area of teeth roots in the oral cavity of a living animal comprising the steps of:
    softening said calculus by applying from a syringe through a needle passage having a diameter on the order of 0.009 inch without clogging the passage to said subgingival area a viscous oral gel composition comprising
        an effective amount of water,
        from about 0.01 to about 5.0 percent by weight of a calculus endotoxin solvating surfactant having a molecular weight of from about 150 to about 250
        from about 0.4 to about 1.5 percent by weight calcium chelator, and
    scaling and debriding said softened calculus from said subgingival area with a scaling tip after said oral gel composition has been applied to said subgingival area for at least 2 minutes, whereby said softened calculus and endotoxin are readily removed from said subgingival.

12. The method of claim 11 wherein said gel composition further comprises sodium bicarbonate.

13. The method of claim 11 wherein said gel composition further comprises an antimicrobial agent.

14. The method of claim 11 wherein said gel composition further comprises from about 0.1 to about 10 percent by weight of an agent effective to increase significantly the viscosity of said composition.

15. The method of claim 11 wherein said surfactant comprises from 0.05 to 0.75 percent by weight of said composition and said calcium chelator comprises from about 0.4 to about 1.5 percent by weight of said composition.

16. A method to remove calculus and endotoxin from a subgingival area of teeth in the oral cavity of a living animal comprising the steps of:
    applying from an ultrasonic scaling tip passage having a diameter on the order of 0.009 inch without clogging the passage to said area a liquid oral composition comprising:
        an effective amount of water,
        from about 0.01 to about 5.0 percent by weight of a calculus and endotoxin solvating surfactant having a molecular weight of from about 150 to about 250,
        from about 0.1 to about 5.0 percent by weight calcium chelator, and
    scaling and debriding said area while said oral composition is being applied to said area, whereby calculus and endotoxin are removed from said area.

17. The method of claim 16 wherein said liquid composition further comprises sodium bicarbonate.

18. The method of claim 16 wherein said liquid composition further comprises an antimicrobial agent.

19. The method of claim 16 wherein said calcium chelator comprises from about 0.4 to about 1.5 percent by weight of said composition.

20. The method of claim 16 wherein said surfactant comprises from 0.05 to 0.75 percent by weight of said composition.

21. A method for scaling and debriding teeth in the oral cavity of a living animal to remove hard calculus from a subgingival area of said teeth comprising the steps of:
    softening said hard calculus by applying through passage having a diameter on the order of 0.009 inch without clogging the passage to said area, a liquid oral composition comprising:
        an effective amount of water, from about 0.01 to about 5.0 percent by weight of a calculus solvating surfactant having a molecular weight of from about 150 to about 250, from about 0.4 to about 1.5 percent by weight calcium chelator, and scaling and debriding said softened calculus from said area with an ultrasonic scaling tip, whereby said softened calculus is removed from said area.

22. The method of claim 21 wherein said composition further comprises sodium bicarbonate.

23. The method of claim 21 wherein said composition further comprises an antimicrobial agent.

24. The method of claim 21 wherein said calcium chelator comprises from about 0.4 to about 1.5 percent by weight of said composition.

25. The method of claim 21 wherein said surfactant comprises from 0.05 to 0.75 percent by weight of said composition.

26. A method of using liquid for scaling and debriding to remove calculus and endotoxin from a subgingival area of teeth roots in the oral cavity of a living animal comprising the steps of:

softening said calculus by applying through an ultrasonic scaling tip passage of about 0.009 inch diameter without clogging the passage to said subgingival area a liquid oral composition comprising an effective amount of water, from about 0.01 to about 5.0 percent by weight of a calculus endotoxin solvating surfactant having a molecular weight of from about 150 to about 250 from about 0.4 to about 1.5 percent by weight calcium chelator, and scaling and debriding said softened calculus from said subgingival area with said scaling tip, whereby said softened calculus and endotoxin are readily removed from said subgingival.

27. The method of claim 26 wherein said composition further comprises sodium bicarbonate.

28. The method of claim 26 wherein said composition further comprises an antimicrobial agent.

29. The method of claim 26 wherein said calcium chelator comprises from about 0.4 to about 1.5 percent by weight of said composition.

30. The method of claim 26 wherein said surfactant comprises from 0.05 to 0.75 percent by weight of said composition.

31. The method of claim 6, 11 or 21 wherein said composition further comprises hydroxyethyl cellulose and polymixin B.

32. The method of claim 1, 6, 11, 16 or 26 wherein said calcium chelator is ethylene diamine tetra acetic acid disodium salt.

33. The method of claim 1, 6, 11, 16 or 26 wherein said surfactant comprises sodium lauryl sulfate.

34. A method of removing calculus from a subgingival area of a tooth in the oral cavity of a living animal, comprising:

subgingivally applying an oral gel composition through a needle passage to said area, said oral gel composition comprising effective amounts of water, surfactant, and calcium chelator, scaling said area whereby calculus is removed from said area.

35. The method of claim 34 further comprising debriding said area.

36. The method of claim 34 further comprising removing endotoxin from a area.

37. The method of claim 34 wherein said scaling is after said composition has been applied to said area for at least about 2 minutes.

38. The method of claim 34 wherein said surfactant is adapted to solvate calculus and endotoxin.

39. The method of claim 34 wherein said calcium chelator comprises from about 0.1 top about 5.0 percent by weight of said composition.

40. The method of claim 34 wherein said surfactant comprises from about 0.1 top about 5.0 percent by weight of said composition.

41. The method of claim 34 wherein said surfactant has a molecular weight of from about 150 to about 250.

42. The method of claim 34 wherein said passage has a diameter on the order of about 0.009 inch.

43. The method of claim 34 wherein said surfactant comprises from about 0.1 top about 5.0 percent by weight of said composition, said surfactant is adapted to solvate calculus, and said calculus is removed from said area after about 2 minutes.

* * * * *